(12) United States Patent
Kierkels et al.

(10) Patent No.: US 6,964,863 B2
(45) Date of Patent: Nov. 15, 2005

(54) PROCESS FOR THE PREPARATION OF 2,4-DIDEOXYHEXOSES AND 2,4,6-TRIDEOXYHEXOSES

(75) Inventors: Joannes Gerardus Theodorus Kierkels, Sittard (NL); Daniel Mink, Eupen (BE); Sven Panke, Zurich (CH)

(73) Assignee: DSM IP Assets B.V., Te Heerlen (NL)

( * ) Notice: Subject to any disclaimer, the term of this patent is extended or adjusted under 35 U.S.C. 154(b) by 10 days.

(21) Appl. No.: 10/481,303

(22) PCT Filed: Jul. 9, 2002

(86) PCT No.: PCT/NL02/00450

§ 371 (c)(1),
(2), (4) Date: Dec. 19, 2003

(87) PCT Pub. No.: WO03/006656

PCT Pub. Date: Jan. 23, 2003

(65) Prior Publication Data

US 2004/0171125 A1 Sep. 2, 2004

(30) Foreign Application Priority Data

Jul. 12, 2001 (NL) .............................................. 1018525
Dec. 20, 2001 (NL) .............................................. 1019622

(51) Int. Cl.$^7$ ........................... C12P 19/02; C12P 17/06
(52) U.S. Cl. ....................................... 435/105; 435/125
(58) Field of Search ................................. 435/105, 125

(56) References Cited

U.S. PATENT DOCUMENTS

| | | | |
|---|---|---|---|
| 5,594,153 A | 1/1997 | Thottathil et al. | 549/374 |
| 5,795,749 A | 8/1998 | Wong et al. | 435/105 |

FOREIGN PATENT DOCUMENTS

WO WO 00/08011 2/2000

OTHER PUBLICATIONS

Chen et al., J Am Chem Soc (1992) 114(2):741–748.
Gesson et al., Tetrahedron Lett (1989) 30(47):6503.
Gijsen et al., J Am Chem Soc (1994) 116(8):8422–8423.
Gijsen et al., J Am Chem Soc (1995) 117(29):7585–7591.
Griffith et al., J Chem Soc Chem Commun (1987) p. 1625.
International Search Report mailed on Jul. 18, 2002, for PCT patent application No. PCT/NL02/00450 filed on Jul. 9, 2002, 4 pages.
Kozlowski et al., Carbohydrate Res (1997) 300:301.
Lankhorst, Pharmacopeial Forum 22(3):2414–2422.
Watanabe et al., Bioorg & Med Chem (1997) 5(2):437–444.
Wong et al., J Am Chem Soc (1995) 117(11):3333–3339.
Greenberg et al., PNAS (2004) 101(16):5788–5793.

*Primary Examiner*—Bernard Dentz
(74) *Attorney, Agent, or Firm*—Morrison & Foerster LLP

(57) ABSTRACT

The invention relates to a process for the preparation of a 2,4-dideoxyhexose or a 2,4,6-trideoxyhexose from a substituted or unsubstituted carbonyl compound with at least 2 carbon atoms and at least one α-hydrogen atom and a substituted or unsubstituted aldehyde in the presence of an aldolase and water, the reaction between the substituted or unsubstituted carbonyl compound with at least 2 carbon atoms and at least one α-hydrogen atom and the substituted or unsubstituted aldehyde being carried out at a carbonyl concentration of at most 6 moles/l of reaction mixture and the final concentration of the 2,4-dideoxyhexose or the 2,4,6-trideoxyhexose being at least 2 mass % of the reaction mixture. The invention also relates to the use of a 2,4-dideoxyhexose or a 2,4,6-trideoxyhexose obtained by means of a process according to the invention in the preparation of a medicine, particularly in the preparation of a statine.

13 Claims, No Drawings

PROCESS FOR THE PREPARATION OF 2,4-DIDEOXYHEXOSES AND 2,4,6-TRIDEOXYHEXOSES

CROSS-REFERENCE TO RELATED APPLICATION

This application is the national phase of PCT application PCT/NL02/00450 having an international filing date of 9 Jul. 2002, and claims priority from Dutch patent application No. 1018525, filed 12 Jul. 2001, and from Dutch patent application No. 1019622 filed 20 Dec. 2001. The contents of these documents are incorporated herein by reference.

The invention relates to a process for the preparation of a 2,4-dideoxyhexose or a 2,4,6-trideoxyhexose from a substituted or unsubstituted carbonyl compound with at least 2 carbon atoms and at least one α-hydrogen atom and a substituted or unsubstituted aldehyde in the presence of an aldolase and water.

Such a process is known from U.S. Pat. No. 5,795,749, which describes the synthesis of 2,4,6-trideoxyhexoses via a 4-substituted 3-hydroxybutanal intermediate. Use is made of acetaldehyde and a 2-substituted aldehyde as reactants and of an aldolase as catalyst.

A known disadvantage of such enzyme catalyzed aldol condensations is that the production capacity is low. This is particularly due to the fact that such aldol condensations are generally carried out at low aldehyde concentrations, since it was generally assumed that the aldolase used would to a high extent be inactivated at higher aldehyde concentrations. Another disadvantage of the low concentrations used is that at the end of the reaction the concentration of the 2,4,6-trideoxyhexose in the reaction mixture is low, which strongly influences the costs of for example purification. As a consequence it was not to be expected that it would be possible to develop a commercially attractive process for the preparation of 2,4-dideoxyhexoses and 2,4,6-trideoxyhexoses on the basis of such a technology.

The invention provides a commercially attractive process for the preparation of a 2,4-dideoxyhexose or a 2,4,6-trideoxyhexose by means of an enzyme catalyzed aldol condensation.

This is accomplished according to the invention by carrying out the reaction between the substituted or unsubstituted carbonyl compound with at least 2 carbon atoms and least one α-hydrogen atom and the substituted or unsubstituted aldehyde at a carbonyl concentration of at most 6 moles/l of reaction mixture, such that the final concentration of the 2,4-dideoxyhexose or the 2,4,6-trideoxyhexose is at least 2 mass % of the reaction mixture.

In the known process for the synthesis of 2,4-dideoxyhexoses and 2,4,6-trideoxyhexoses carbonyl concentrations of at most 0.4 mole per liter reaction mixture are applied. Final concentrations of the 2,4-dideoxyhexose or the 2,4,6-trideoxyhexose are obtained that are at most around 1 mass % of the reaction mixture. Surprisingly, the applicant has found that carbonyl concentrations of up to 6 moles/l can suitably be applied, while the degree of enzyme deactivation remains limited despite the high carbonyl concentration. As a result, higher final concentrations of the 2,4-dideoxyhexose or the 2,4,6-trideoxyhexose can be obtained, so that the production capacity is increased and the costs of, inter alia, purification of the product are lowered. As a consequence it proved to be possible to develop a commercially attractive process.

In the framework of the invention carbonyl concentration is understood to be the sum of the concentrations of the substituted or unsubstituted carbonyl compounds with at least 2 carbon atoms and at least one α-hydrogen atom, the substituted or unsubstituted aldehyde and the intermediate product which is formed in the reaction of the substituted or unsubstituted carbonyl compound with at least 2 carbon atoms and at least one α-hydrogen atom with the substituted or unsubstituted aldehyde.

The carbonyl concentration is in essence held at a value below 6 moles/l during the synthesis process. It will be clear to one skilled in the art that slightly higher concentrations for a (very) short time will have little adverse effect, and therefore are still admissible within the framework of the invention. Preferably the carbonyl concentration lies between 0.1 and 5 moles per liter of reaction mixture, more preferably between 0.6 and 4 moles per liter of reaction mixture.

The final concentration of the 2,4-dideoxyhexose or the 2,4,6-trideoxyhexose in practice generally lies between 5 and 50 mass %, for example between 8 and 40 mass %, in particular between 10 and 35 mass %, calculated relative to the reaction mixture at the end of the reaction.

The sequence of addition of the substituted or unsubstituted carbonyl compound with at least 2 carbon atoms and at least one α-hydrogen atom, the substituted or unsubstituted aldehyde and the aldolase is not very critical. Preferably the aldolase is added to the reaction mixture before the addition of the substituted or unsubstituted carbonyl compound with at least 2 carbon atoms and at least one α-hydrogen atom. More preferably the aldolase is mixed with a solution of at least a part of the substituted or unsubstituted aldehyde before the substituted or unsubstituted carbonyl compound with at least 2 carbon atoms and at least one α-hydrogen atom is added, particularly when, under the chosen conditions, the substituted or unsubstituted aldehyde that is used reacts with itself to a lesser degree than the substituted or unsubstituted carbonyl compound with at least 2 carbon atoms and at least one α-hydrogen atom that is used. Preferably more than 0.1 mole/l of reaction mixture of the substituted or unsubstituted aldehyde is supplied, more preferably more than 0.3 mole per liter of reaction mixture, in particular more than 0.6 mole per liter of reaction mixture. This choice of the initial concentration of the substituted or unsubstituted aldehyde has a favourable effect on the initial reaction rate of the enzymatic process. Aldolase can be added or metered during the reaction in several portions.

In one embodiment of the invention both the substituted or unsubstituted carbonyl compound with at least 2 carbon atoms and at least one α-hydrogen atom and the substituted or unsubstituted aldehyde and the aldolase are each added to the reaction mixture in one go. In doing so, the substituted or unsubstituted carbonyl compound with at least 2 carbon atoms and at least one α-hydrogen atom, the substituted or unsubstituted aldehyde and the aldolase can be added both at the same time and in succession. According to this embodiment the sum of the added quantities of substituted or unsubstituted carbonyl compound with at least 2 carbon atoms and at least one α-hydrogen atom and substituted or unsubstituted aldehyde can generally amount to up to 6 moles per liter of reaction mixture and in practice final product concentrations between 7 and 15 mass %, in particular between 5 and 20 mass % of the reaction mixture are usually achieved.

In another embodiment of the invention the addition of the substituted or unsubstituted carbonyl compound with at least 2 carbon atoms and at least one α-hydrogen atom and/or the substituted or unsubstituted aldehyde is carried out in at least two portions, each following addition taking place after at least a part of the reactants from the preceding addition has been converted. This makes it possible for the sum of the quantities of substituted or unsubstituted carbonyl compound with at least 2 carbon atoms and at least one α-hydrogen atom and substituted or unsubstituted aldehyde added in the course of the reaction to amount to more than 6 moles per liter of reaction mixture, while at the same time the carbonyl concentration in the reaction mixture at any point of time during the reaction is lower than 6 moles/l to limit inactivation of the enzyme. The aldolase can if desired be added in one go or in at least two portions.

In yet another embodiment the substituted or unsubstituted carbonyl compound with at least 2 carbon atoms and at least one α-hydrogen atom and/or the substituted or unsubstituted aldehyde are metered into the reaction mixture in time during the reaction. Preferably in this embodiment at least a part of the substituted or unsubstituted aldehyde is supplied together with the aldolase. The aldolase can if desired be added in one go, be added in several portions or be metered in time.

The last two embodiments can lead to final concentrations of the 2,4-dideoxyhexose or the 2,4,6-trideoxyhexose which are higher than 40 mass %. Furthermore it has been found that metering into the reaction mixture of the substituted or unsubstituted carbonyl compound with at least 2 carbon atoms and at least one α-hydrogen atom, the substituted or unsubstituted aldehyde and/or the aldolase can lead to considerable savings on the enzyme costs.

Combinations of the above embodiments are also possible.

The reaction temperature and the pH are not very critical and both are chosen as a function of the substrate. Preferably the reaction is carried out in the liquid phase. The reaction can be carried out for example at a reaction temperature between −5 and 45° C., preferably between 0 and 10° C. and a pH between 5.5 and 9, preferably between 6 and 8.

The reaction is preferably carried out at more or less constant pH, use for example being made of a buffer or of automatic titration. As a buffer for example sodium and potassium bicarbonate, sodium and potassium phosphate, triethanolamine/HCl, bis-tris-propane/HCl and HEPES/KOH can be applied. Preferably a potassium or sodium bicarbonate buffer is applied, for example in a concentration between 20 and 400 mmoles/l of reaction mixture.

The molar ratio between the total quantity of substituted or unsubstituted carbonyl compound with at least 2 carbon atoms and at least one α-hydrogen atom that is added and the total quantity of substituted or unsubstituted aldehyde that is added is not very critical and preferably lies between 1.5:1 and 4:1, in particular between 1.8:1 and 2.2:1. Other ratios can also be applied but offer no advantages.

As catalyst in the process according to the invention use is made of an aldolase that catalyzes the aldol condensation between two aldehydes or between an aldehyde and a ketone. Preferably the aldolase used is 2-deoxyribose-5-phosphate aldolase (DERA, EC 4.1.2.4) or mutants hereof, more preferably DERA from *Escherichia coli* or mutants hereof. The quantity of DERA to be used is not very critical and is chosen as a function of for example the reactants applied, the reactant concentrations, the desired reaction rate, the desired duration of the reaction and other economic factors. The quantity of DERA to be used lies between for example 50 and 5000 U/mmole of the substituted or unsubstituted aldehyde. 1 U (unit) is a measure of the enzymatic activity and corresponds to the conversion of 1 μmole of 2-deoxyribose-5-phosphate per minute at 37° C.

The substituted or unsubstituted carbonyl compound with at least 2 carbon atoms and at least one α-hydrogen atom preferably has 2–6 carbon atoms, more preferably 2–4 carbon atoms. Use can for example be made of aldehydes, for example acetaldehyde and propanal, and ketones, for example acetone and fluoroacetone. When an aldehyde is used as substituted or unsubstituted carbonyl compound with at least two carbon atoms and at least one α-hydrogen atom, it may of course also be applied in the form of its (hemi)acetal, for example as acetal of an alcohol, in particular methanol, ethanol or glycol.

As substituted or unsubstituted aldehyde use can be made for example of aldehydes with 2–20 carbon atoms, for example acetaldehyde, propanal, butanal, an acetal-protected dialdehyde or a substituted aldehyde, in particular a substituted acetaldehyde with the formula HC(O)CH$_2$X where X represents a group that is identical to or can be converted into the substituent required in the end product, for example a CN group, or a substituent that can be split off as a leaving group in a subsequent reaction, for example a halogen, in particular Cl, Br or I; a tosylate group; a mesylate group; an acyloxy group, in particular an acetoxy group; a phenacetyloxy group; an alkyloxy group or an aryloxy group, chloroacetaldehyde being particularly suitable.

The substituted or unsubstituted acetaldehyde may be applied as such or in the form of its (hemi)acetal, for example as acetal of an alcohol such as methanol, ethanol or glycol.

The 2,4-dideoxyhexose or 2,4,6-trideoxyhexose with formula 1 is

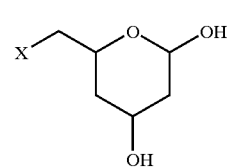

(1)

for example a desired intermediate product in the preparation of various medicines, in particular for the synthesis of HMG-CoA reductase inhibitors, more in particular for the synthesis of statines, for example lovastatine, cerivastatine, rosuvastatine, simvastatine, pravastatine and fluvastatine, in particular for ZD-4522 as described in Drugs of the future, (1999), 24(5), 511–513 by M. Watanabe et al., Bioorg. & Med. Chem. (1997), 5(2), 437–444. The invention therefore provides a new, economically attractive route to 2,4-dideoxyhexoses or 2,4,6-trideoxyhexoses that can be used for the synthesis of for example 2-(6-hydroxymethyl-1,3-dioxane-4-yl)acetic acid, which is a desired intermediate product for the preparation of medicines, in particular statines.

The 2,4-dideoxyhexose or 2,4,6-trideoxyhexose with formula 1 can be prepared with the aid of the process according to the invention from acetaldehyde and HC(O)CH$_2$X, where X is as defined above, and can subsequently be converted, for example via known methods, into the corresponding 4-hydroxy-tetrahydropyran-2-one with formula 2,

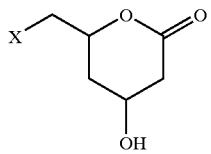

(2)

where X is as defined above. Suitable reagents for this conversion are for example $Br_2$ with as base calcium carbonate (Tetrahedron Lett. 30 (47), 1989 p. 6503), pyridinium dichromate in dichloromethane (Carbohydrate Res. 300 1997 p. 301) and tetra-N-propylammoniumtetraoxoruthenate (J. Chem. Soc, Chem. Commun. 1987 p. 1625).

The 4-hydroxy-tetrahydropyran-2-one obtained can subsequently if desired be converted into a 2-(1,3-dioxane-4-yl) acetic acid derivative with formula 3,

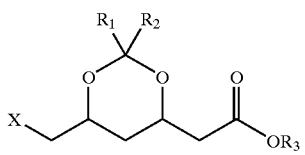

(3)

where X is as defined above and $R_1$, $R_2$ and $R_3$ each independently represent an alkyl group with 1–3 carbon atoms. This conversion can for example be effected in the presence of a suitable acetalation agent and an acid catalyst.

Subsequently the 2-(1,3-dioxane-4-yl) acetic acid derivative can be hydrolyzed in the presence of a base and water to form a salt with formula 4,

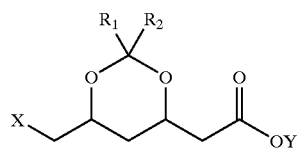

(4)

where Y stands for an alkali metal, an earth alkali metal, or a substituted or unsubstituted ammonium group, preferably Na, Ca or a tetraalkylammonium compound and where X, $R_1$ and $R_2$ are as defined above. The hydrolysis can be followed by conversion into the corresponding 2-(1,3-dioxane-4-yl) acetic acid according to formula 4 with Y=H.

The salt of the 2-(1,3-dioxane-4-yl) acetic acid according to formula 4 can be converted into a corresponding ester of the 2-(1,3-dioxane-4-yl) acetic acid according to formula 3 with X, $R_1$ and $R_2$ as defined above and in which $R_3$ represents an alkyl group with 1–12 carbon atoms, an aryl group with 6–12 carbon atoms or an aralkyl group with 7–12 carbon atoms in a way known per se. Preferably the salt of the 2-(1,3-dioxane-4-yl) acetic acid is converted into the corresponding t-butylester of the 2-(1,3-dioxane-4-yl) acetic acid.

The 2-(1,3-dioxane-4-yl) acetic acid derivative with formula 3, in which $R_3$ represents an alkyl group with 1–12 carbon atoms, an aryl group with 6–12 carbon atoms or an aralkyl group with 7–12 carbon atoms can be converted into the acetic acid derivate of the corresponding 2-(6-hydroxymethyl-1,3-dioxane-4-yl) acetic acid with formula 5, in which $R_1$, $R_2$ and $R_3$ are as defined above, for example as described in U.S. Pat. No. 5,594,153

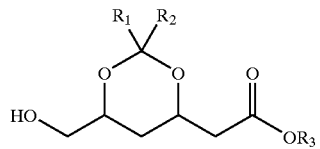

(5)

or in WO-A-200008011, via conversion into a compound according to formula 3 with X=acyloxy, for example an acetoxy group, and $R_1$, $R_2$ and $R_3$ are as defined above, followed by replacement of the acyloxy group, in a way generally known, by a hydroxyl group.

The 4-hydroxy-tetrahydropyran-2-one with formula 2

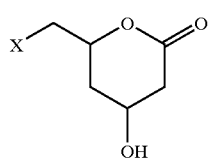

(2)

where X is as defined above, can be also converted into the corresponding dihydroxyhexanoic acid with formula 6 with the aid of an acid or a base.

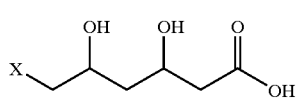

(6)

The dihydroxyhexanoic acid with formula 6 can subsequently be converted into a 2-(1,3-dioxane-4-yl) acetic acid derivative with formula 3, in which X, $R_1$, $R_2$ and are as defined above and $R_3$ represents an alkyl group with 1–12 carbon atoms, an aryl group with 6–12 carbon atoms or an aralkyl group with 7–12 carbon atoms, for example in the presence of a suitable acetalation agent and an acid catalyst.

The invention will be elucidated on the basis of the examples, without however being limited thereby.

EXAMPLES

Preparation and Measurement Methods

1. Preparation of a Quantity of 6-chloro-2,4,6-trideoxyhexose as Reference Material for GC Analysis 76 mL (0.60 mole) of a 50% chloroacetaldehyde solution and 84 mL (1.47 moles) acetaldehyde were added to 0.62 L 100 mM NaHCO3 solution at 10° C. after which the pH was adjusted to pH 7.0 with the aid of 4N NaOH. The enzymatic reaction was started by addition of 220 g enzyme solution (2050 U/g). After about 18 hours' stirring a maximum conversion into 6-chloro-2,4,6-trideoxyhexose was measured via GC. The reaction was stopped by adding 1.7 L acetone. 4 g dicalite was added to this mixture and after approximately 30 minutes' stirring the mixture was filtered. The filtrate was evaporated for 5 hours at 40° C. under vacuum. The resulting oil was purified by means of column chromatography on a silica gel column (400 mL) and eluted with an eluent consisting of a mixture of petroleum ether (boiling point: 40–70° C.) and ethyl acetate in a volume ratio of 1:2. After evaporation of the fraction with an Rf value of 0.33, in total 26 g of the 6-chloro-2,4,6-trideoxyhexose was isolated. The term Rf value of a fraction is known to one skilled in the art and is defined as the distance that a fraction covers in the column divided by the distance covered by the mobile solvent in the column or the time that a fraction needs to cover a particular distance in the column divided by the time that the mobile solvent needs to cover that same distance in the column.

The purity of the 6-chloro-2,4,6-trideoxyhexose was determined by means of 1H-NMR in accordance with a method described by P. P. Lankhorst in Pharmacopeial Forum, 22, (3), 2414–2422.

2. GC Analysis

The concentration of the 6-chloro-2,4,6-trideoxyhexose during the enzymatic reaction was determined by means of gas chromatographic analysis. Use was made of a Hewlett Packard GC with flame ionization detector, type HP5890 series II, provided with a Chrompack CP-Sil 5 CB column (25 m*0.25 mm, $d_f$ 1.2 µm). Concentrations were determined on the basis of a calibration curve of the 6-chloro-2, 4,6-trideoxyhexose with known chemical purity (1) in acetone.

3. Preparation of the DERA Solution

Standard techniques were applied to overexpress the DERA enzyme in recombinant *Escherichia coli* cells. Such techniques are described in Sambrook et al, "Molecular Cloning: A Laboratory Manual", Cold Spring Harbor, N.Y., 1989. In this case the deoC gene of *Escherichia coli* W3110 was cloned in the commercially available expression vector pBADMyc-HisB (Invitrogen, Groningen, NL). The gene (including the stop codon) was multiplied by means of a polymerase chain reaction and introduced into the NcoI and EcoRI sites of the vector in such a way that the ATG start codon of deoC was equal to the ATG codon on the NcoI site of the vector (translation fusion). Because the deoC stop codon was also cloned, the formation of a fusion protein with the His tag, which is also coded on the vector, was prevented. *Escherichia coli* DH10B cells (Life Technologies, Breda, NL) with the resulting plasmide pBAD DERA2.2 were cultivated in a 10 L aerated and stirred tank reactor on a complex Luria Bertani medium with 100 µg/mL carbenicillin and induced by addition of arabinose to 0.01%. To increase the cell density, two extra aqueous solutions containing pure glycerol (feed 1) and 13% yeast extract and 1.3% trypton (Difco, Mich., US) (feed 2) were added after the cells had consumed the LB medium. In this way approximately 350 g wet cells were obtained from a 10 L culture, which were recovered by means of centrifuging, following which they were resuspended in a potassium phosphate buffer of pH 7.2 and again centrifuged. The supernatant was removed after which the pellet was stored at −20° C.

In the literature different processes are described for the purification of DERA from recombinant *E. Coli* cells, for example in Chen et al., J. Am. Chem. Soc. Vol 114, 1992, 741–748 and Wong et al., J. Am. Chem. Soc. Vol 117, 1995, 3333–3339). Purification, however, is not a condition for efficient use of DERA in aldol reactions, see for example Wong et al., J. Am. Chem. Soc. Vol 117, 1995, 3333–3339. For the partial purification of DERA standard techniques were applied. Frozen pellets were suspended in a 100 mM potassium phosphate buffer at pH 7.2 (1 part by weight of wet cells and 2 parts by weight of buffer), after which the cell walls were destroyed by means of continuous ultrasonification. The clear crude extract was obtained by means of centrifuging and was directly used or stored at −20° C. The solution can be concentrated further if desired by means of ultrafiltration, for example with the aid of Millipore ultrafiltration membranes with a cut-off value of 10,000 Dalton (Millipore, Bedford, USA). Typical specific activities that were obtained by means of this process are between 1400 and 5300 units per g of solution.

4. Determination of the Activity of DERA

Recombinant *E. coli* cells that synthesize DERA were subjected to sonification in a 50 mM potassium phosphate buffer and centrifuged (18,500 rpm, 30 min.) to remove the cell material. The resulting free cell extract was diluted and used in a linked spectrophotometric test. In this test 2-deoxyribose-5-phosphate was converted into D-glyceraldehyde-3-phosphate and acetaldehyde, after which the D-glyceraldehyde-3-phosphate was converted into dihydroxyacetone phosphate in the presence of triosephosphate isomerase (TIM, EC 5.3.1.1). Dihydroxyacetone phosphate was then converted into glycerol-3-phosphate in the presence of glycerol phosphate dehydrogenase (GDH, EC 1.1.1.8). In the last step nicotineamine adenine dinucleotide was consumed in reduced form (NADH), which was monitored spectrophotometrically via determination of the decrease in absorption at 340 nm. Typically a total volume of 3 ml was applied, containing 2878.5 µM of a 50 mM triethanolamine buffer with pH 7.2, 30 µl of a 12 mM solution of NADH in water, 11.5 µL of an enzyme suspension containing 30 units of GDH and 500 units of TIM in 3.2M aqueous ammonium phosphate, and 30 µL of a 50 mM solution of 2-deoxyribose-5-phosphate in water. The reaction was started by adding 50 µl free cell extract. The temperature was 37° C. The activity, expressed in U (nits), with 1 unit being equal to the enzymatic activity that corresponds to the conversion of 1 µmole of 2-deoxyribose-5-phosphate per minute at 37° C., was calculated from the linear decrease in the absorption at 340 nm.

Example I

Preparation of 6-chloro-2,4,6-trideoxyhexose in a Batch Experiment 4.3 mL (0.03 mole) of a 45% solution of chloroacetaldehyde and 3.4 mL (0.06 mole) acetaldehyde were added to 37 mL of a 100 mM buffer solution of NaHCO$_3$ at a temperature of 4° C. The pH of this mixture was 7.3. The enzymatic reaction was started by addition of 6.3 mL (5270 U/g) enzyme solution. The reaction was carried out at a constant pH of 7.5. At regular intervals the mixture was analyzed by means of GC. The reaction was stopped by addition of 100 mL acetone after a concentration of the 6-chloro-2,4,6-trideoxyhexose of approximately 80 g/L (8 mass %) had been reached.

Example II

Preparation of 6-chloro-2,4,6-trideoxyhexose in a Repetitive Batch Experiment

The experiment from example I was repeated. However, after the concentration of the 6-chloro-2,4,6-trideoxyhexose reached approximately 80 g/L, another 4.3 mL (0.03 mole) of a 45% solution of chloroacetaldehyde, 3.4 mL (0.06 mole) acetaldehyde and 6.3 mL (5270 U/g) enzyme solution were again added. This was repeated three more times, each time after the conversion had reached a constant value and did not increase any further. In this way in total 0.15 mole of a 45% solution of chloroacetaldehyde and 0.30 mole acetaldehyde were added. The reaction was carried out at a constant pH of 7.5. Samples from the reaction mixture were analyzed with the aid of GC. The final 6-chloro-2,4,6-trideoxyhexose concentration was around 240 g/L (24 mass %).

Example III

Preparation of 6-chloro-2,4,6-trideoxyhexose by Means of Metering of the Reaction Components.

84 g (1.0 mole) NaHCO$_3$ was added to 6.2 L demineralized water after which the solution was cooled to around 2° C. Subsequently 72.3 mL (0.4 mole) of a 45% solution of chloroacetaldehyde was added to this, after which the pH of the solution was adjusted to 7.3 with the aid of 32% HCl. An enzyme solution ($6.8 \times 10^6$ U) was added to this mixture, after which the volume was made up to 7.5 L. In 2 hours in total 1.3 L (9.5 moles) of a 45% chloroacetaldehyde solution and 0.9 L (9.9 moles) of a 50% acetaldehyde solution were metered to this mixture. After this, in 5 hours 0.86 L (9.5 moles) of a 50% acetaldehyde solution was added. The reaction mixture was stirred overnight at 2° C. and a constant pH of 7.5. The total weight of the reaction mixture amounted to 10.9 kg. The 6-chloro-2,4,6-trideoxyhexose content was determined by means of gas chromatography and was found to be 126 g/L (12.6 mass %).

Example IV
Preparation of 6-chloro-2,4,6-trideoxyhexose by Means of Metering of the Reaction Components.

11.8 g (0.14 mole) $NaHCO_3$ was added to 0.44 L demineralized water after which the solution was cooled to around 2° C. Subsequently 10.0 mL (0.07 mole) of a 45% solution of chloroacetaldehyde was added to this, after which the pH of the solution was adjusted to 7.3 with the aid of 32% HCl. An enzyme solution ($1.03 \times 10^6$ U) was added to this mixture. In 2 hours 0.193 L (1.35 moles) of a 45% chloroacetaldehyde solution and 0.127 L (1.40 moles) of a 50% acetaldehyde solution were metered to this mixture. After this, in 5 hours 0.134 L (1.46 moles) of a 50% acetaldehyde solution was added. The reaction mixture was stirred overnight at 2° C. at a constant pH of 7.5. The 6-chloro-2,4,6-trideoxyhexose content was determined by means of gas chromatography and was found to be 180 g/L (18.0 mass %).

What is claimed is:

1. A process for the preparation of a 2,4-dideoxyhexose or a 2,4,6-trideoxyhexose which process comprises providing a reaction mixture comprising a substituted or unsubstituted carbonyl compound containing at least 2 carbon atoms and at least one α-hydrogen atom and a substituted or unsubstituted aldehyde in the presence of an aldolase and water, wherein the carbonyl concentration is at most 6 moles/liter of the reaction mixture, and the final concentration of the 2,4-dideoxyhexose or the 2,4,6-trideoxyhexose is at least 2 mass % of the reaction mixture.

2. The process of claim 1, wherein the final concentration of the 2,4-dideoxyhexose or the 2,4,6-trideoxyhexose is 5 to 50 mass % of the reaction mixture.

3. The process of claim 2, wherein the final concentration of the 2,4-dideoxyhexose or the 2,4,6-trideoxyhexose is 10 to 35 mass % of the reaction mixture.

4. The process of claim 1, wherein the carbonyl concentration in the reaction mixture is 0.6 to 4 moles/liter of the reaction mixture.

5. The process of claim 1, wherein the reaction mixture comprises at least 0.1 mole/liter of the substituted or unsubstituted aldehyde.

6. The process of claim 1, wherein the substituted or unsubstituted carbonyl compound containing at least 2 carbon atoms and at least one α-hydrogen atom and/or the substituted or unsubstituted aldehyde are added to the reaction mixture in at least two portions.

7. The process of claim 1, wherein the substituted or unsubstituted carbonyl compound containing at least 2 carbon atoms and at least one α-hydrogen atom and/or the substituted or unsubstituted aldehyde are metered to the reaction mixture over time.

8. The process of claim 1, wherein the molar ratio between the total quantity of substituted or unsubstituted carbonyl compound containing at least 2 carbon atoms and at least one α-hydrogen atom that is added and the total quantity of substituted or unsubstituted aldehyde that is added lies between 1.5:1 and 4:1.

9. The process of claim 1, wherein the aldolase comprises a 2-deoxyribose-5-phosphate aldolase.

10. The process of claim 9, wherein the 2-deoxyribose-5-phosphate aldolase is derived from *Escherichia coli*.

11. The process of claim 1, wherein the substituted or unsubstituted aldehyde is a substituted aldehyde of the formula $HC(O)CH_2X$, where X represents CN, a halogen, a tosylate group, a mesylate group, an acyloxy group, a phenacetyloxy group, an alkyloxy group or an aryloxy group.

12. The process of claim 11, wherein X is a leaving group.

13. The process of claim 1, wherein the substituted or unsubstituted carbonyl compound is acetaldehyde.

* * * * *